United States Patent [19]

Conley

[11] Patent Number: 4,645,836

[45] Date of Patent: Feb. 24, 1987

[54] PROCESS FOR THE PREPARATION OF 6,7-DIHYDROXY-4-ALKYL-2(1H) QUINAZOLINONE-1-PROPIONIC ACIDS

[75] Inventor: Richard A. Conley, Annandale, N.J.

[73] Assignee: Ortho Pharmaceutical Corporation, Raritan, N.J.

[21] Appl. No.: 531,138

[22] Filed: Sep. 12, 1983

[51] Int. Cl.$^4$ ............................................ C07D 239/80
[52] U.S. Cl. ...................................... 544/286; 562/452
[58] Field of Search ........................................... 544/286

[56] References Cited

U.S. PATENT DOCUMENTS 3,983,119  9/1976  Beverung, Jr. et al. ............ 544/286

FOREIGN PATENT DOCUMENTS 53-34783   3/1978   Japan .................................... 544/286
55-141472 11/1980  Japan .................................... 544/286
2063263    6/1981   United Kingdom ................ 544/286

OTHER PUBLICATIONS

Morrison et al., *Organic Chemistry*, Sec. Ed., 1966, Allyn & Bacon, Inc., Boston, pp. 748–751.

Primary Examiner—Glennon H. Hollrah
Assistant Examiner—James H. Turnipseed
Attorney, Agent, or Firm—Benjamin F. Lambert

[57] ABSTRACT

A process for the preparation of 6,7-dihydroxy-4-alkyl-2(1H) quinazolinone-1-propionic acids is described. The propionic acid compounds are renal vasodilators and thereby increase renal blood flow. They are useful as cardiovascular agents.

4 Claims, No Drawings

PROCESS FOR THE PREPARATION OF 6,7-DIHYDROXY-4-ALKYL-2(1H) QUINAZOLINONE-1-PROPIONIC ACIDS

The present invention relates to a process for preparing 6,7-dihydroxy-4-alkyl-2(1H)quinazolinone-1-propionic acids and their pharmaceutically acceptable salts. The 1-propionic acid compounds which can be prepared by the present process have the following formula:

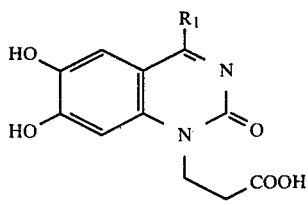

wherein $R_1$ is a lower alkyl group having 1-5 carbon atoms.

The 1-propionic acids can be prepared according to the following scheme:

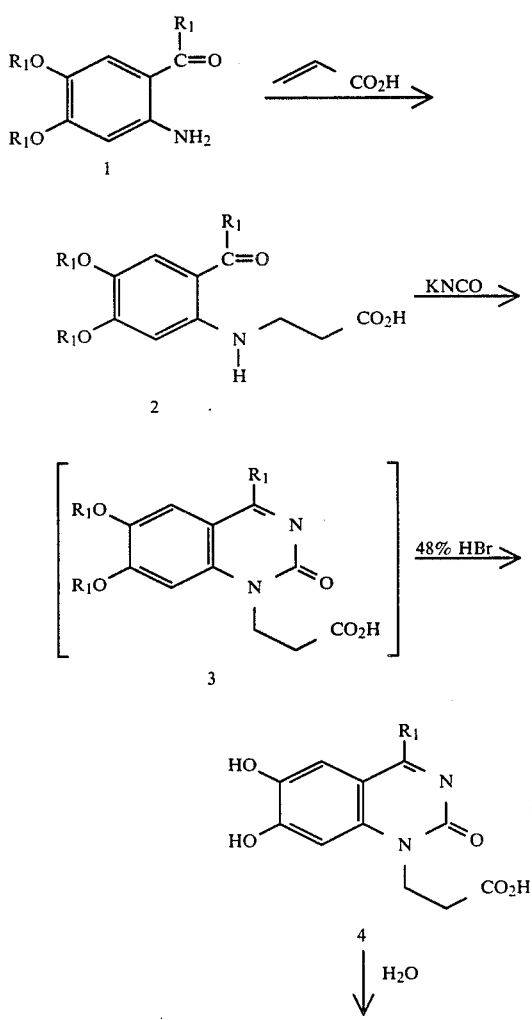

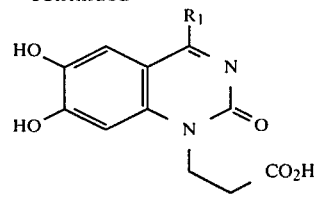

As can be seen from the reaction scheme a substituted alkylphenyl ketone (1) is reacted with acrylic acid to give the corresponding β-alanine derivative (2). Suitable alkylphenyl ketones which can be employed include acetophenone, propiophenone and the like. The reaction can be carried out neat or in a suitable solvent at a temperature between about 70°-100° C. The preferred temperature range is about 80°-90° C. It is preferred to use an excess of the acrylic acid during this reaction step. When a solvent is employed for the alkylation step solvents such as acetic acid and propionic acid may be employed. The β-alanine derivative (2) is converted directly to the acid salt (4) by first reacting it with an alkali metal cyanate such as potassium cyanate or sodium cyanate to give the cyclized intermediate (3) and then reacting the intermediate (3) in situ with a hydrohalo acid such as hydrobromic or hydriodic acid. The initial reaction is carried out in the presence of a solvent such as acetic acid or propionic acid. Alternatively, the intermediate can be isolated and purified prior to cleaving the alkoxy group which is then cleaved by reacting the compound with a hydrohalo acid to form the acid salt (4). The acid salt can be obtained in good yield by preferably refluxing the reaction mixture for several hours. Other agents which may be employed to cleave the alkoxy group include aluminum chloride, boron tribromide and pyridine hydrochloride. The acid salt (4) is then converted to the free acid by the addition of water. The free acid is purified by techniques known to those skilled in the art.

The 6,7-dihydroxy-4-alkyl-2(1H)quinazolinone-1-propionic acids are renal vasodilators. As such they increase renal blood flow and are therefore useful as cardiovascular agents.

The following examples describe the invention in greater particularity and are intended as a means of illustrating but not limiting the invention.

EXAMPLE 1

N-(2-acetyl-4,5-dimethoxyphenyl)-β-alanine

A mixture of 2-amino-4,5-dimethoxyacetophenone (910 g, 4.66 mol), acrylic acid (730 ml., 10.67 mol), and acetic acid (2100 ml) was heated at 90° C. for 2 hours. Following treatment with Darco and hot filtration, the product was precipitated by the addition of water (2475 ml) over a 1 hour period. The reaction mixture was cooled and the product was filtered and washed with cold distilled water (4×90 ml) and cold methanol (1×600 ml). Drying under vacuum at 60° C. gave 1049 g (84%) of the product as a yellow powder, mp 149.5°-151.5° C. NMR (CDCl$_3$) δ 2.50 (s, 3H, Ar-COC$\underline{H}_3$), 2.73 (t, 2H, C$\underline{H}_2$—CO$_2$H), 3.57 (t, 2H, N—C$\underline{H}_2$), 3.82 (s, 3H, C$\underline{H}_3$OAr), 3.93 (s, 3H, C$\underline{H}_3$OAr), 6.18 (s, 1H, Ar$\underline{H}$), 7.13 (s, 1H, Ar$\underline{H}$), 10.05 (broad s, 2H, NH, COOH).

EXAMPLE 2

6,7-Dihydroxy-4-methyl-2(1H)quinazolinone-1-propionic Acid, Hydrobromide Salt A slurry of N-(2-acetyl-4,5-dimethoxyphenyl)-β-alanine (600 g, 2.24 mol) in glacial acetic acid (3000 ml) was prepared and potassium cyanate (236.8 g, 2.92 mol) was added to the slurry. The reaction mixture was stirred for 2 hours and then heated at 45°-50° C. for an additional 2 hours. Following the addition of aqueous HBr (6000 ml, 48%), the reaction was refluxed for 40 hours. The product precipitated upon cooling and the reaction mixture was then cooled in an ice-water bath. The product was filtered and washed with aqueous acetic acid (50%, 2×600 ml, 1×300 ml). Drying under vacuum at 90°-100° C. gave 497 g (63%) of the product as a yellow powder, mp 258.0°-260.0° C. dec. NMR (TFA) δ 3.13 (s, 3H, C$\underline{H}_3$), 3.18 (t [overlapped by singlet at 3.13] 2H, C$\underline{H}_2$CO$_2$CH), 4.85 (t, 2H, NC$\underline{H}_2$), 7.52 (s, 1H, Ar$\underline{H}$), 7.83 (s, 1H, Ar$\underline{H}$).

When in the above procedure N-(2-acetyl-4,5-diethoxyphenyl)-β-alanine, N-(2-acetyl-4,5-dipropoxyphenyl)-β-alanine and N-(2-propionyl-4,5-dimethoxyphenyl)-β-alanine are employed in place of N-(2-acetyl-4,5-dimethoxyphenyl)-β-alanine, the corresponding 6,7-dihydroxy-4-methyl-2(1H)quinazolinone-1-propionic acid hydrobromide salt and 6,7-dihydroxy-4-ethyl-2(1H)quinazolinone-1-propionic acid hydrobromide salt are obtained.

EXAMPLE 3

6,7-Dihydroxy-4-methyl-2(1H)quinazolinone-1-propionic Acid

A slurry of 6,7-dihydroxy-4-methyl-2(1H)quinazolinone-1-propionic acid hydrobromide salt (2.22 kg, 6.27 mol) in distilled water (8.5 l) was prepared and stirred at room temperature for 1 hour. The reaction mixture was cooled, filtered and the product was washed with cold distilled water (2×2.2 l) and cold isopropanol (2×1.1 l). Drying under vacuum at 80°-110° C. gives 1.57 kg (93.5%) of the free acid as a yellow powder, mp 350.0°-306.0° C. dec. NMR (TFA) δ 3.10 (s, 3H, C$\underline{H}_3$), 3.17 (t [overlapped by singlet at 3.10], 2H, C$\underline{H}_2$CO$_2\underline{H}$), 4.85 (t, 2H, NC$\underline{H}_2$), 7.40 (s, 1H, Ar$\underline{H}$), 7.73 (s, 1H, Ar$\underline{H}$).

When in the above procedure the 6,7-dihydroxy-4-ethyl-2(1H)quinazolinone-1-propionic acid hydrobromide salt, 6,7-dihydroxy-4-propyl-2(1H)quinazolinone-1-propionic acid hydrobromide salt and 6,7-dihydroxy-4-butyl-2(1H)-quinazolinone-1-propionic acid hydrobromide salt are employed in place of the 6,7-dihydroxy-4-methyl-2(1H)quinazolinone-1-propionic acid hydrobromide salt, the corresponding 6,7-dihydroxy-4-ethyl-2(1H)quinazolinone-1-propionic acid, 6,7-dihydroxy-4-propyl-2(1H)quinazolinone-1-propionic acid, and 6,7-dihydroxy-4-butyl-2(1H)quinazolinone-1propionic acid are obtained.

What is claimed is:

1. A process for the preparation of compounds of the formula

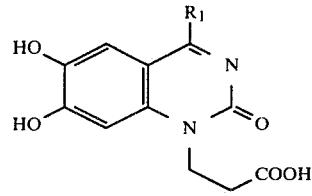

which comprises reacting an amino ketone of the formula

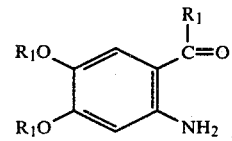

with acrylic acid to form a β-alanine of the formula

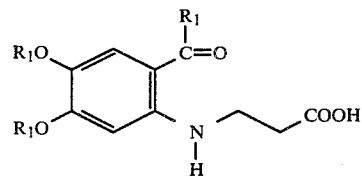

cyclizing the β-alanine with an alkali metal cyanate to give a quinazolinone of the formula

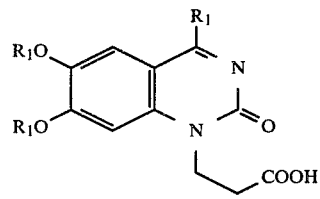

hydrolyzing the ether groups with a hydrohalo acid to form a salt of the formula

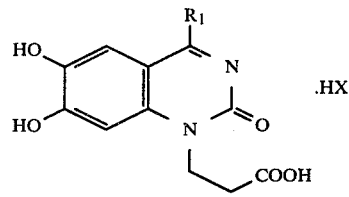

and treating the salt with water to form the free acid, wherein R$_1$ is lower alkyl and X is selected from hydrobromic acid and hydriodic acid.

2. The process of claim 1 wherein R$_1$ is methyl.
3. The process of claim 1 wherein the hydrohalo acid is hydrobromic acid.
4. The process of claim 1 wherein the alkali metal cyanate is potassium cyanate.

* * * * *